United States Patent [19]

Dostert et al.

[11] 4,329,466

[45] May 11, 1982

[54] CERTAIN NOR-TROPAN-8-AMINE-3-ARYL OR HETEROARYL DERIVATIVES

[75] Inventors: Philippe L. Dostert, Paris; Thierry F. Imbert, Noisy le Roi; Bernard P. Bucher, Marnes la Coquette, all of France

[73] Assignee: Delalande S.A., Courbevoie, France

[21] Appl. No.: 254,684

[22] Filed: Apr. 16, 1981

Related U.S. Application Data

[62] Division of Ser. No. 110,067, Jan. 7, 1980.

[30] Foreign Application Priority Data

Jan. 16, 1979 [FR] France .................................. 79 00971
Dec. 26, 1979 [FR] France .................................. 79 31656

[51] Int. Cl.$^3$ ........................................... C07D 451/02
[52] U.S. Cl. .................................... 546/125; 544/320; 544/321; 546/124

[58] Field of Search ................................. 546/125, 124

[56] References Cited

U.S. PATENT DOCUMENTS 2,838,714  6/1958  Bernstein et al. ................... 546/125

*Primary Examiner*—Alan L. Rotman
*Attorney, Agent, or Firm*—Blanchard, Flynn, Thiel, Boutell & Tanis

[57] ABSTRACT

There are disclosed nor-tropane derivatives substituted at the 3 position with aroylamino or heteroaroylamino and substituted at the 8 position with benzyl, substituted benzyl, 2-methyl thiophene, 3-methyl thiophene, 2-methyl furan or cyclohexylmethyl. The compounds are prepared by condensing the carboxylic acids corresponding to said aroyl or heteroaroyl group with the corresponding β-3-amino-8-substituted nor-tropanes. The compounds possess neuroleptic properties.

6 Claims, No Drawings

CERTAIN NOR-TROPAN-8-AMINE-3-ARYL OR HETEROARYL DERIVATIVES

This is a division of application Ser. No. 110,067 filed Jan. 7, 1980.

The present invention relates to novel nor-tropane derivatives and particularly novel 3-aroylamino and 3-heteroaroylamino nor-tropanes, substituted in position 8, a process for preparing same and their application in therapeutics.

These new derivatives comply more precisely with the formula:

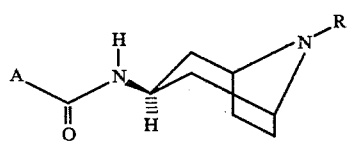

in which R represents:
either a benzyl nucleus, in which case A—CO— designates:
a 5-pyrimidinyl carbonyl nucleus of formula:

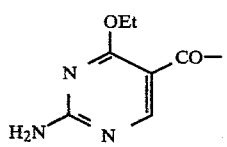

an aroyl nucleus of formula:

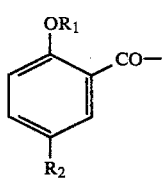

in which the pair ($R_1$, $R_2$) assumes any one of the following values: ($CH_3$, H), ($CH_3$, F), ($CH_3$, $NO_2$), ($CH_3$, OH);
an aroyl nucleus of formula:

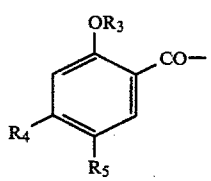

in which the set ($R_3$, $R_4$, $R_5$) assumes any one of the following values: ($CH_3$, $NH_2$, Br), ($CH_3$, $CH_3CONH$, Br), ($CH_3$, $CF_3CONH$, Br), ($CH_3$, $CH_3CONH$, Cl), ($CH_3$, $CF_3CONH$, Cl), ($C_2H_5$, $NH_2$, Br), ($CH_3$, $NH_2$, H), ($CH_3$, $CH_3O$, $CH_3O$), ($CH_3$, $CH_3O$, H);
an aroyl nucleus polysubstituted by the following groups or atoms: dimethoxy-2,3; dimethoxy-3,5; trimethoxy-2,3,4; methoxy-2 dibromo-3,5 amino-4;
or a benzyl nucleus monosubstituted in the meta position of formula:

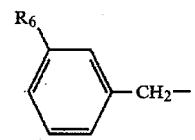

in which $R_6$ represents a methyl or trifluoromethyl group or a halogen atom, in which case A—CO— designates the 2-methoxy 4-amino 5-bromo benzoyl nucleus of formula:

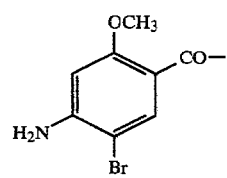

or a benzyl nucleus monosubstituted in the para position of formula:

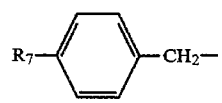

in which $R_7$ represents:
a methyl or methoxy group or an atom of bromine or chlorine, in which case A—CO— represents the 2-amino 4-methoxy 5-pyrimidinyl carbonyl nucleus of formula:

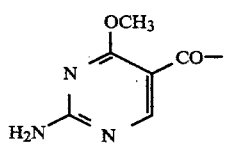

a lower alkyl or a trifluoromethyl group or an atom of chlorine, bromine or fluorine, in which case A—CO— represents a 2-methoxy 4-amino 5-bromo benzoyl nucleus,
or a 3,4-dichloro benzyl group, a 2-methyl thiophene group

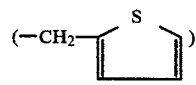

or a 3-methyl thiophene group

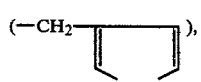

in which case A—CO— represents a 2-methoxy 4-amino 5-bromo benzoyl nucleus;
or a 2-methyl thiophene, a 3-methyl thiophene or a 2-methyl furane group

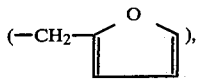

in which case A—CO— represents a 2-methoxy 4-amino 5-chloro benzoyl nucleus;

or a cyclohexylmethyl group, in which case A—CO— represents a 2-methoxy 4-amino 5-bromo benzoyl nucleus.

It should be noted that in formula (I), the chain A—CO—NH is in the equatorial position and the nor-tropanes having such a substituent in the equatorial position will be called β in what follows.

The present invention comprises of course as well the pharmaceutically acceptable mineral or organic acids addition salts of said compounds.

The compounds of formula (I) are obtained by condensing, by the mixed anhydrides method, the acids of formula:

in which A—CO— has the same meanings as A—CO— in formula (I), with the corresponding β-3-amino nor-tropanes of formula:

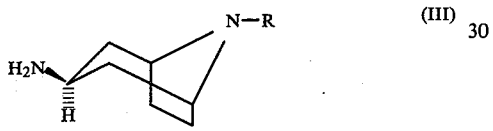

in which R has the same meaning as in formula (I).

The compounds of formula (II) complying more precisely with the particular formula:

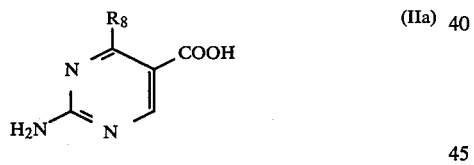

in which R₈ represents a methoxy or an ethoxy group, are new and are obtained by saponification of the compound of formula:

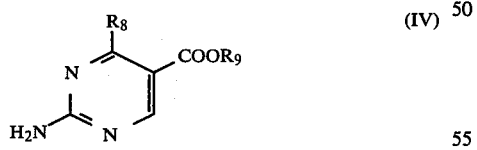

in which R₈ has the same meanings as in formula (IIa) and R₉ represents a methyl or ethyl group.

The compounds of formula (IV) in which the couple (R₈, R₉) assumes the following values: (OCH₃, CH₃) and (OC₂H₅, C₂H₅) are also new and are obtained by a 3-stage synthesis which consists in treating 2-amino 5-ethoxycarbonyl 4-hydroxy pyrimidine, in solution in a basic organic solvent, such as pyridine, with an acid anhydride (e.g. acetic anhydride), then in reacting the product thus obtained with a chlorinating agent preferably phosphorous oxychloride, and finally in causing to react on the resulting raw product, sodium methylate or ethylate, respectively in solution in methanol or ethanol.

The compound of formula (III) in which R represents the benzyl group is new and results from the reduction, by means of sodium in amyl alcohol, of the oxime of N-benzyl nor-tropine-3 one of formula:

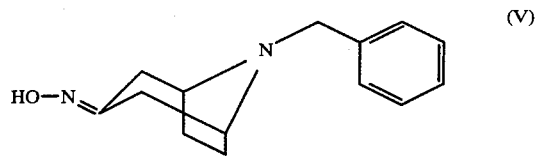

The compounds of formula (III) in which R has the same meanings as in formula (I), with the exception of the benzyl group, are also new and are obtained by a two-stage synthesis which consists in condensing cyclohexylmethyl chloride, 3,4-dichloro benzyl chloride, 2-chloromethyl thiophene, 3-chloromethyl thiophene, 2-chloromethyl furane or the chlorides of formulae:

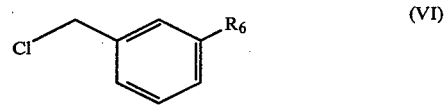

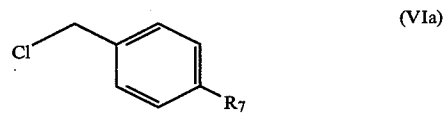

in which R₆ and R₇ have the same meanings as in formula (I), on the compounds of formula:

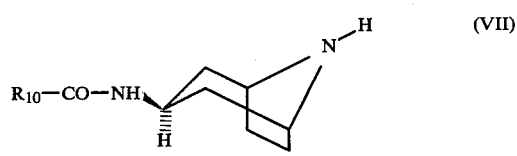

in which R₁₀ represents the methyl or ethoxy group, this condensation being preferably carried out at reflux in an organic solvent such as acetone, acetonitrile or DMF in the presence of potassium carbonate or triethylamine, then in hydrolyzing the acetyl or carbethoxy group.

The compounds of formula (VII), which are new, are obtained by a two-stage synthesis consisting in treating the compound of formula (III) in which R represents the benzyl group, with acetyl chloride or ethyl chloroformiate, in a tetrahydrofurane medium and in the presence of an organic base such as pyridine or triethylamine, then in hydrogenolyzing the product obtained, for example in the presence of palladium on charcoal at 10% in an ethanol medium, at a temperature of 60° C. and at a pressure of 15 bars.

The compounds of formula (I) where the motif A—CO— represents the group of formula:

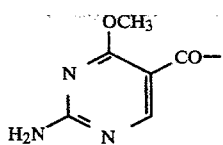

and wherein R is different from the benzyl group, may also be obtained by condensation of the compounds of formula (VIa) with the compound of formula:

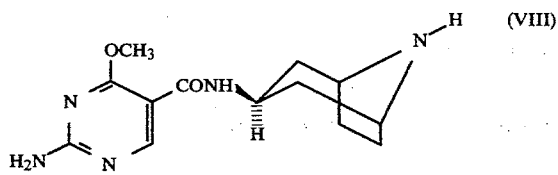

This condensation is preferably carried out in accordance with a process identical to the one used for synthesis of the compounds of formula (III) where R is different from the benzyl group.

Finally, the compound of formula (VIII), also new, is obtained by hydrogenolysis—preferably in an acid medium, in the presence of palladium on charcoal at 10%, at room temperature, at a pressure of 90 mbars and in an alcohol medium—of the compound of formula:

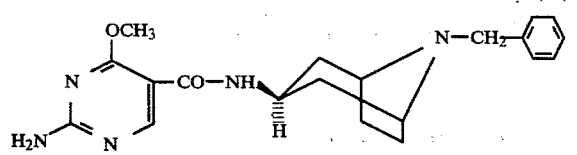

This latter compound is prepared in accordance with the process described above for the preparation of the compounds of formula (I) [mixed anhydrides method] by condensing acid of formula:

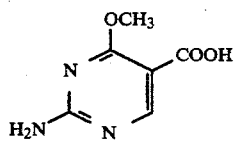

with the compound of formula (III) wherein R is a benzyl group.

The acid addition salts of the compounds of formula (I) may be obtained by usual methods. For example the acid, e.g. hydrochloric, oxalic, maleic or fumaric acid, is added to the compounds of formula (I) in base form, in the presence of an appropriate solvent such as ethanol for example.

The following preparations are given by way of examples to illustrate the invention.

EXAMPLE 1

β-3-[(4-amino 5-bromo 2-methoxy) benzoyl] amino N-parafluorobenzyl nor-tropane, chlorhydrate (I)

Code number: 19

To a solution of 8.35 g of 4-amino 5-bromo 2-methoxy benzoic acid (II) in 200 ml of tetrahydrofurane cooled to 0° C., were added 5.18 ml of triethylamine, then 3.5 ml of ethyl chloroformiate. After 45 minutes at 0° C., 8.6 g of β-3-amino N-parafluorobenzyl nor-tropane [(III), prepared as in example 5, code No. 103] were added and left to agitate for .3 hours. The solvent was evaporated, the residue taken up in methylene chloride, washed with carbonated water, then with water, dried on sodium sulfate, filtered and the solvent evaporated. The residue was crystallized in isopropylic ether. It was filtered and the precipitate obtained (12.9 g) was dissolved in 150 ml of ethanol; chlorhydric ethanol ≃6.5 N was added, the precipitate obtained was filtered, rinsed with ether on the filter and recrystallized in absolute alcohol. 5 g of the expected product were obtained.

Yield: 36%
Melting point: >265° C.
Molecular weight: 498.82
Empirical formula: $C_{22}H_{26}BrClFN_3O_2$
Elementary analysis:

|  | C | H | N |
|---|---|---|---|
| Calculated (%) | 52.97 | 5.25 | 8.42 |
| Obtained (%) | 52.91 | 4.93 | 8.26 |

By the same process, but from the corresponding reagents, the compounds of the formula (I) appearing in table I below were obtained.

TABLE I

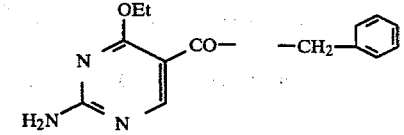

| Code No. | A—CO— | R | Form | Empirical formula | Molecular weight | Melting point (°C.) |
|---|---|---|---|---|---|---|
| 3 | OEt (pyrimidine-CO—) | —CH$_2$—Ph | maleate | $C_{25}H_{31}N_5O_6$ | 497.54 | 217 |

TABLE I-continued

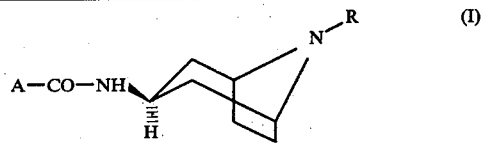

| # | A | R | form | Formula | MW | mp |
|---|---|---|---|---|---|---|
| 8 | (OMe, CO-, guanidino pyrimidine) | -CH₂-C₆H₄-Cl | base | $C_{20}H_{24}ClN_5O_2$ | 401.89 | 185 |
| 9 | " | -CH₂-C₆H₄-OMe | base | $C_{21}H_{27}N_5O_3$ | 397.47 | 180 |
| 10 | " | -CH₂-C₆H₄-CH₃ | base | $C_{21}H_{27}N_5O_2$ | 381.47 | 178 |
| 16 | (OMe, CO-, H₂N-, Br phenyl) | -CH₂-C₆H₅ | base | $C_{22}H_{26}BrN_3O_2$ | 444.36 | 209 |
| 19 | (OMe, CO-, H₂N-, Br phenyl) | -CH₂-C₆H₄-F | HCl | $C_{22}H_{26}BrClFN_3O_2$ | 498.82 | >260 |
| 20 | " | -CH₂-C₆H₄-Br | Base | $C_{22}H_{25}Br_2N_3O_2$ | 523.26 | 223 |
| 21 | " | -CH₂-C₆H₄-CF₃ | Base | $C_{23}H_{25}BrF_3N_3O_2$ | 529.36 | 165 |
| 22 | " | -CH₂-C₆H₄-Cl | base | $C_{22}H_{25}BrClN_3O_2$ | 478.81 | 216 |
| 23 | " | -CH₂-C₆H₄-CH₃ | " | $C_{23}H_{28}BrN_3O_2$ | 458.39 | 217 |
| 24 | " | -CH₂-C₆H₄-CH₃ (meta) | " | $C_{23}H_{28}BrN_3O_2$ | " | 192 |
| 25 | " | -CH₂-C₆H₄-Cl (meta) | Base | $C_{22}H_{25}BrClN_3O_2$ | 478.81 | 189 |
| 26 | " | -CH₂-C₆H₄-F (meta) | base | $C_{22}H_{25}BrFN_3O_2$ | 462.35 | 167 |
| 27 | " | -CH₂-C₆H₄-Br (meta) | " | $C_{22}H_{25}Br_2N_3O_2$ | 523.26 | 204 |
| 28 | " | -CH₂-C₆H₃-Cl₂ | " | $C_{22}H_{24}BrCl_2N_3O_2$ | 513.26 | 193 |
| 29 | " | -CH₂-thienyl | Base | $C_{20}H_{24}BrN_3O_2S$ | 450.39 | 213 |
| 30 | " | -CH₂-C₆H₄-Et | base | $C_{24}H_{30}BrN_3O_2$ | 472.41 | 182 |
| 32 | " | -CH₂-thienyl | " | $C_{20}H_{24}BrN_3O_2S$ | 450.39 | 220 |
| 33 | " | -CH₂-C₆H₄-CF₃ | Base | $C_{23}H_{25}BrF_3N_3O_2$ | 512.36 | 201 |

TABLE I-continued $$\text{A—CO—NH} \cdots \bigcirc \!\!\!-\!\!\! \text{N} \diagdown \text{R} \quad \text{(I)}$$

| No. | A—CO— | R | Salt | Formula | MW | mp |
|---|---|---|---|---|---|---|
| 35 | " | —CH₂—cyclohexyl | Maleate + 4/5 H₂O | C₂₆H₃₆BrN₃O₆ + 4/5 H₂O | 566.48 | 160 |
| 37 | 2-amino-5-methoxy-pyrimidine-CO— (H₂N-pyrimidine with OMe, CO—) | —CH₂—C₆H₄—Br | HCl | C₂₀H₂₅BrClN₅O₂ | 482.81 | 230 |
| 40 | CH₃CONH—, OMe, Br substituted phenyl-CO— | —CH₂—C₆H₅ | HCl + 1/6 H₂O | C₂₄H₂₉BrClN₃O₃ + 1/6 H₂O | 543.88 | 217 |
| 41 | CF₃CONH—, OMe, Br phenyl-CO— | " | Base | C₂₄H₂₅BrF₃N₃O₃ | 540.37 | 191 |
| 42 | CH₃CONH—, OMe, Cl phenyl-CO— | " | " | C₂₄H₂₈ClN₃O₃ | 441.94 | 180 |
| 43 | CF₃CONH—, OMe, Cl phenyl-CO— | " | base | C₂₄H₂₅ClF₃N₃O₃ | 495.92 | 181 |
| 48 | O₂N—, OMe phenyl-CO— | " | " | C₂₂H₂₅N₃O₄ | 395.44 | 138 |
| 49 | F—, OMe phenyl-CO— | " | Base | C₂₂H₂₅N₂FO₂ | 368.44 | 96 |
| 51 | HO—, OMe phenyl-CO— | " | " | C₂₂H₂₆N₂O₃ | 366.44 | 195 |
| 60 | MeO—, MeO—, OMe phenyl-CO— | " | base | C₂₄H₃₀N₂O₄ | 410.49 | 130 |
| 61 | MeO—, MeO—, OMe, (N?) phenyl-CO— | " | HCl + 3/5 H₂O | C₂₄H₃₁ClN₄O₂ + 3/5 H₂O | 457.77 | 220 |
| 62 | OMe phenyl-CO— | " | HCl + 1/5 H₂O | C₂₂H₂₇ClN₂O₂ + 1/5 H₂O | 390.51 | >260 |
| 64 | MeO, OMe phenyl-CO— | " | Base + ⅔ H₂O | C₂₃H₂₈N₂O₃ + ⅔ H₂O | 392.48 | 78 |
| 67 | H₂N—, OMe phenyl-CO— | " | base | C₂₂H₂₇N₃O₂ | 365.46 | 145 |

TABLE I-continued $$A-CO-NH\underset{H}{\overset{}{\diagdown}} \text{[bicyclic]} N-R \quad (I)$$

| Code No. | A | R | Salt | Formula | MW | mp |
|---|---|---|---|---|---|---|
| 68 | 2,4-(MeO)₂-C₆H₃-CO— | " | HCl | $C_{23}H_{29}ClN_2O_3$ | 416.93 | 209 |
| 71 | 4-H₂N-2-MeO-C₆H₃-CO— | 2-furyl-ethyl | Base | $C_{20}H_{24}ClN_3O_3$ | 389.87 | 220 |
| 72 | 4-H₂N-5-Cl-2-MeO-C₆H₂-CO— | " | " | $C_{20}H_{24}ClN_3O_2S$ | 405.94 | 227 |
| 73 | " | 2-thienyl-ethyl | Base | $C_{20}H_{24}ClN_3O_2S$ | 405.94 | 215 |
| 74 | 4-H₂N-3,5-Br₂-2-MeO-C₆H-CO— | benzyl | HCl + 1.2 H₂O | $C_{22}H_{26}Br_2ClN_3O_2$ + 1.2 H₂O | 581.35 | 208 |
| 75 | 4-H₂N-5-Br-2-EtO-C₆H₂-CO— | " | fumarate | $C_{27}H_{32}BrN_3O_6$ | 574.46 | 212 |
| 83 | 3,5-(MeO)₂-C₆H₃-CO— | —CH₂—C₆H₅ | base | $C_{23}H_{28}N_2O_3$ | 380.47 | 182 |

| Code No. | Yield (%) | | ELEMENTARY ANALYSIS | | |
|---|---|---|---|---|---|
| | | % | C | H | N |
| 3 | 62 | Cal. | 60.35 | 6.28 | 14.08 |
| | | Obt. | 60.08 | 6.25 | 14.13 |
| 8 | 62 | Cal. | 59.97 | 6.02 | 17.43 |
| | | Obt. | 59.69 | 6.00 | 17.35 |
| 9 | 65 | Cal. | 63.45 | 6.85 | 17.62 |
| | | Obt. | 63.66 | 7.10 | 17.66 |
| 10 | 71 | Cal. | 66.12 | 7.13 | 18.36 |
| | | Obt. | 66.20 | 7.15 | 78.31 |
| 16 | 65 | Cal. | 59.46 | 5.90 | 9.46 |
| | | Obt. | 59.37 | 6.00 | 9.66 |
| 19 | 36 | Cal. | 52.97 | 5.25 | 8.42 |
| | | Obt. | 52.91 | 4.93 | 8.26 |
| 20 | 67 | Cal. | 50.49 | 4.82 | 8.03 |
| | | Obt. | 50.68 | 4.67 | 7.86 |
| 21 | 72 | Cal. | 53.91 | 4.92 | 8.20 |
| | | Obt. | 53.85 | 4.68 | 8.05 |
| 22 | 70 | Cal. | 55.18 | 5.26 | 8.78 |
| | | Obt. | 55.12 | 5.24 | 8.86 |
| 23 | 71 | Cal. | 60.26 | 6.16 | 9.17 |
| | | Obt. | 60.44 | 6.13 | 9.27 |
| 24 | 64 | Cal. | 60.26 | 6.16 | 9.17 |
| | | Obt. | 60.28 | 6.41 | 9.23 |
| 25 | 58 | Cal. | 55.18 | 5.26 | 8.78 |
| | | Obt. | 55.48 | 5.11 | 8.77 |
| 26 | 55 | Cal. | 57.15 | 5.45 | 9.09 |
| | | Obt. | 57.43 | 5.29 | 9.01 |
| 27 | 78 | Cal. | 50.49 | 4.82 | 8.03 |
| | | Obt. | 50.58 | 4.79 | 8.27 |
| 28 | 76 | Cal. | 51.48 | 4.71 | 8.19 |
| | | Obt. | 51.67 | 4.77 | 8.40 |
| 29 | 54 | Cal. | 53.33 | 5.37 | 9.33 |
| | | Obt. | 53.15 | 5.26 | 9.40 |
| 30 | 81 | Cal. | 61.01 | 6.40 | 8.90 |
| | | Obt. | 60.92 | 6.45 | 8.98 |
| 32 | 67 | Cal. | 53.33 | 5.37 | 9.33 |
| | | Obt. | 53.40 | 5.44 | 9.31 |
| 33 | 58 | Cal. | 53.92 | 4.92 | 8.20 |

TABLE I-continued $$A-CO-NH\overset{\underset{H}{|}}{\diagdown}\diagup\diagdown\diagup N^{R} \quad (I)$$

| | | | C | H | N |
|---|---|---|---|---|---|
| 35 | 48 | Cal. | 53.76 | 6.52 | 7.23 |
| | | Obt. | 53.74 | 4.93 | 8.33 |
| | | Obt. | 53.50 | 6.16 | 7.33 |
| 37 | 51 | Cal. | 49.75 | 5.22 | 14.51 |
| | | Obt. | 49.56 | 5.15 | 14.58 |
| 40 | 54 | Cal. | 52.99 | 5.81 | 7.73 |
| | | Obt. | 53.25 | 5.61 | 7.76 |
| 41 | 90 | Cal. | 53.34 | 4.66 | 7.78 |
| | | Obt. | 53.64 | 4.92 | 7.92 |
| 42 | 63 | Cal. | 65.22 | 6.39 | 9.51 |
| | | Obt. | 64.99 | 6.69 | 9.34 |
| 43 | 63 | Cal. | 58.12 | 5.08 | 8.47 |
| | | Obt. | 58.35 | 5.35 | 8.60 |
| 48 | 77 | Cal. | 66.82 | 6.37 | 10.63 |
| | | Obt. | 66.59 | 6.55 | 10.79 |
| 49 | 81 | Cal. | 71.71 | 6.84 | 7.60 |
| | | Obt. | 71.60 | 7.10 | 7.65 |
| 51 | 57 | Cal. | 72.10 | 7.15 | 7.65 |
| | | Obt. | 72.29 | 7.42 | 7.62 |
| 60 | 73 | Cal. | 70.22 | 7.37 | 6.82 |
| | | Obt. | 70.07 | 7.18 | 6.72 |
| 61 | 57 | Cal. | 62.97 | 7.09 | 6.12 |
| | | Obt. | 63.26 | 7.11 | 6.08 |
| 62 | 61 | Cal. | 68.29 | 7.03 | 7.24 |
| | | Obt. | 67.78 | 7.36 | 7.46 |
| 64 | 85 | Cal. | 70.38 | 7.50 | 7.14 |
| | | Obt. | 70.23 | 7.39 | 7.04 |
| 67 | 47 | Cal. | 72.30 | 7.45 | 11.50 |
| | | Obt. | 72.40 | 7.78 | 11.37 |
| 68 | 53 | Cal. | 66.25 | 7.01 | 6.72 |
| | | Obt. | 66.18 | 7.11 | 6.85 |
| 71 | 51 | Cal. | 61.61 | 6.21 | 10.78 |
| | | Obt. | 61.92 | 6.34 | 11.02 |
| 72 | 58 | Cal. | 59.17 | 5.96 | 10.35 |
| | | Obt. | 59.15 | 5.91 | 10.12 |
| 73 | 47 | Cal. | 59.17 | 5.96 | 10.35 |
| | | Obt. | 59.13 | 5.64 | 10.37 |
| 74 | 36 | Cal. | 45.45 | 4.92 | 7.23 |
| | | Obt. | 45.69 | 4.77 | 7.11 |
| 75 | 45 | Cal. | 56.45 | 5.62 | 7.32 |
| | | Obt. | 56.45 | 5.74 | 7.33 |
| 83 | 91 | Cal. | 72.60 | 7.42 | 7.36 |
| | | Obt. | 72.52 | 7.41 | 7.25 |

EXAMPLE 2

β-3-[5-(2-amino 4-methoxy pyrimidinyl) carbonyl] amino N-parachlorobenzyl nor-tropane (I)

Code number: 8

1st stage: β-3-[5-(2-amino 4-methoxy pyrimidinyl) carbonyl] amino nor-tropane (VIII)

A solution of 148.5 g of maleate of β-3-[5-(2-amino 4-methoxy 4-pyrimidinyl) carbonyl] amino N-benzyl nor-tropane [(I), obtained as in example 1, melting point 185° C., Empirical formula $C_{20}H_{25}N_5O_2+1/6$ $H_2O$, elementary analysis: Cal. (%)-C: 64.84-H: 6.89-N: 18.91: Obt. (%)-C: 64.62-H: 6.86-N: 19.35], in 1,500 ml of alcohol at 50% was hydrogenolyzed in an autoclave at room temperature and at a pressure of 90 mbars, in the presence of 25 g of palladium on charcoal at 10%. It was filtered, the solvent evaporated, the residue crystallized in acetone and recrystallized in alcohol at 90%. 120 g of the desired product were thus isolated.

Yield: 98%
Melting point: 220° C.
Molecular weight: 412.41
Empirical formula: $C_{17}H_{25}N_5O_6+7/5$ $H_2O$
Elementary analysis:

| | C | H | N |
|---|---|---|---|
| Calculated (%) | 48.69 | 6.01 | 16.98 |
| Obtained (%) | 48.97 | 6.19 | 16.84 |

2nd stage: β-3-[5-(2-amino 4-methoxy pyrimidinyl) carbonyl] amino N-parachlorobenzyl nor-tropane (I)

Code number: 8

To a solution of 7 g of succinate of the compound of formula (VIII) previously obtained in 100 ml of acetone were added 9.8 g of potassium carbonate, then 4.28 g of para-chlorobenzyl chloride. Then the mixture was heated to reflux for 39 hours, the solvent was evaporated, the residue was diluted in water and extracted with chloroform. It was dried on sodium sulfate, the solvent was evaporated, the residue was crystallized in isopropylic ether and recrystallized in normal butylic alcohol. 5 g of the expected product were thus obtained.

Yield: 70%
Melting point: 185° C.
Molecular weight: 401.89
Empirical formula: $C_{20}H_{24}ClN_5O_2$
Elementary analysis:

|  | C | H | N |
|---|---|---|---|
| Calculated (%) | 59.77 | 6.02 | 17.43 |
| Obtained (%) | 59.69 | 6.00 | 17.35 |

By the same process, but from the corresponding reagents, the compounds of formula (I) appearing in table I and having code numbers 9, 10, 12 and 37 were obtained.

EXAMPLE 3

5-(2-amino 4-methoxy pyrimidinyl) carboxylic acid (IIa)

Code number: 88

1st stage: 2-amino 4-methoxy 5-methoxycarbonyl pyrimidine (IV)

Code number: 96

50 g of 2-amino 4-hydroxy 5-ethoxycarbonyl pyrimidine were heated to reflux with 40 ml of acetic anhydride in 300 ml of anhydrous pyridine for 2 hours. The reaction medium was then frozen, the precipitate filtered, rinced with acetone and dried. 140 g of the raw product thus obtained (yield 62%) was heated to 60° C. in 900 ml of phosphorous oxychloride for 2 hours. After cooling, 200 ml of ethyl ether were added while stirring; the precipitate formed was then filtered, rinced with ether, then thrown on 1 kg of ice and neutralised with a solution of sodium bicarbonate while stirring. The precipitate was filtered, rinced with water and dried. 112 g of this intermediate (yield 81%) were stirred for 2 hours in a solution of sodium methanolate at 0° C., prepared with 46 g of sodium in 800 ml of anhydrous methanol. Once again at the normal temperature, the precipitate was filtered, rinced with water and dried. 80 g of 2-amino 4-methoxy 5-methoxycarbonyl pyrimidine were obtained.

Yield: 95%

Melting point: 221° C. (Bu OH)

CHLORHYDRATE

Empirical formula: $C_7H_{10}ClN_3O_3$
Molecular weight: 219.631
Melting point: 260° C.
Elementary analysis:

|  | C | H | N |
|---|---|---|---|
| Calculated (%) | 38.28 | 4.59 | 19.13 |
| Obtained (%) | 38.28 | 4.42 | 19.39 |

By the same process, but from the corresponding reagents, the compound of formula (IV) bearing the code number 97: 2-amino 4-ethoxy 5-ethoxycarbonyl pyrimidine was prepared.

Empirical formula: $C_9H_{13}N_3O_3$
Molecular weight: 211.218
Melting point: 190° C. (Bu OH)
NMR (DMSO): δppm
2 triplets centred at 1.3 ppm 6 H ($OCH_2$—$CH_3$)
2 quadruplets centered at 4.3 ppm 4 H (O—$CH_2$—)
1 group centered at 7.2 ppm 2 H ($NH_2$)
1 singleton centered at 8.5 ppm 1 H (heteroatomic)
IR (KBr): $\gamma cm^{-1}$ 3370 $cm^{-1}$($NH_2$)
1680 $cm^{-1}$ ester (COO—$C_2H_5$)

2nd stage: 5-(2-amino 4-methoxy pyrimidinyl)carboxylic acid (IIa)

Code number: 88

600 g of 2-amino 4-methoxy 5-methoxycarbonyl pyrimidine prepared in the preceding stage were heated to 65° C. with agitation for 1 hour in a mixture of 1.5 l of methanol and 1.5 l of NaOH at 5%. Once cooled, the reaction medium was poured on 4 l of iced water then acidifed to pH=3 under stirring with concentrated hydrochloric acid. The 5-(2-amino 4-methoxy pyrimidinyl) carboxylic acid precipitated, drained, washed with acetone then dried was obtained with a yield of 88.5%.

HYDRATED SODIUM SALT

Empirical formula: $C_6H_6N_3O_3Na$, 1.25 $H_2O$
Molecular weight: 213.810
Melting point: 260° C.
Elementary analysis:

|  | C | H | N |
|---|---|---|---|
| Calculated (%) | 33.73 | 4.01 | 19.67 |
| Obtained (%) | 34.05 | 3.73 | 19.84 |

By the same process, but from the corresponding reagents, the compound of formula (IIa) appearing in table II and bearing code number 89, is obtained.

TABLE II structures (IV) and (IIa): pyrimidine ring with $H_2N$ at 2-position, $R_8$ at 4-position, and COOR$_9$ (IV) or COOH (IIa) at 5-position

| Code No. | Formula | $R_8$ | $R_9$ | Empirical formula | Molecular weight | Melting point (°C.) | Yield (%) | Elementary analysis - NMR spectrum - IR spectrum - Thin layer chromatography | | | |
|---|---|---|---|---|---|---|---|---|---|---|---|
|  |  |  |  |  |  |  |  | % | C | H | N |
| 88 | IIa | $OCH_3$ | — | $C_6H_6N_3O_3Na$ + 1.25 $H_2O$ (sodium salt) | 213.81 | 260 | 88.5 | Cal. | 33.73 | 4.01 | 19.67 |
|  |  |  |  |  |  |  |  | Obt. | 34.05 | 3.73 | 19.84 |
| 89 | " | $OC_2H_5$ | — | $C_7H_9N_3O_3$ | 183.17 | 280 | 76 | NMR spectrum ($CF_3COOH$) δ ppm = 4.75; q; and 1.50; t: O—$CH_2$—$CH_3$ 7.5; m; $NH_2$ 8.8; s; (H at 6) | | | |
|  |  |  |  |  |  |  |  | % | C | H | N |

TABLE II-continued

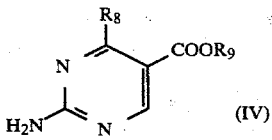

| Code No. | Formula | R8 | R9 | Empirical formula | Molecular weight | Melting point (°C.) | Yield (%) | Elementary analysis - NMR spectrum - IR spectrum - Thin layer chromatography |
|---|---|---|---|---|---|---|---|---|
| 96 | IV | OCH3 | CH3 | C7H10ClN3O3 (chlorhydrate) | 219.63 | 260 | 95 | Cal. 38.28 4.59 19.13<br>Obt. 38.28 4.42 19.39 |
| 97 | " | OC2H5 | C2H5 | C9H13N3O3 | 211.22 | 190 | 92 | NMR (DMSO) δ ppm<br>= 1.3; 2t; 6 H: 2 CH3<br>= 4.3; 2q; 4 H: 2 CH2<br>= 7.2; m; 2 H: NH2<br>= 8.5; s; 1 H at 6<br>IR (KBr) bands NH2 at 3370 cm$^{-1}$<br>and —COOC2H5 at 1680 cm$^{-1}$. |

EXAMPLE 4

β-3-amino N-benzyl nor-tropane, dimaleate (III)

Code number: 98

A suspension of 60 g of N-benzyl nor-tropane oxime (V) in 750 ml of amyl alcohol was heated to 40° C. and 50 g of sodium were introduced at a rate such that the temperature of the reaction mixture rose to 135°–140° C. Then the reaction medium was diluted with 300 ml of water, the organic phase was decanted, and extracted by means of 400 ml of HCl 6 N, and the aqueous phase was washed with isopropylic ether. Then, the aqueous phase was alkalized with concentrated potash, extracted with methylene chloride, dried on sodium sulfate, the solvent was evaporated and the residue distilled. 83 g yield 59%) of liquid, $Eb_{0.15}$=109°–111° C. was obtained which was added to an acetone solution of maleic acid. The precipitate obtained was filtered and recrystallized in absolute alcohol.
Melting point: 150° C.
Empirical formula: C22H28N2O8+4.5 H2O
Molecular weight: 462.87
Elementary analysis:

|  | C | H | N |
|---|---|---|---|
| Calculated (%) | 57.08 | 6.45 | 6.05 |
| Obtained (%) | 57.14 | 6.19 | 5.92 |

NMR SPECTRUM OF THE BASE (CDCl3)

δppm=7.28, m, and 3.53, s, 7H (benzylic) centered on 3.17, m,: 2H (tropanic) at position 1 and 5 centered on 2.82, m,: 1H (tropanic) at position 3 1.52, s, 2 NH2 protons between 2.20 and 1.15, m, 8 tropanic protons (the displacement of the tropanic protons in the presence of Europium salt EU(FOD)3 and particularly of the proton at position 3, as well as the study of the value of the sum of the couplings of the multiplet signal of the proton at 3, in accordance with the law of KARPLUS, showed that proton −3 is at an axial position, this by analogy with the NMR spectra in the presence of Europium of the derivatives α and β-3-amino tropane).

EXAMPLE 5

β-3-amino N-parafluorobenzyl nor-tropane (III)

Code number: 103

1st stage: β-3-acetamido nor-tropane (VII)

To a solution cooled to 0° C. of 96 g of β-3-amino N-benzyl nor-tropane [(III), code number 98, prepared in example 4] in 70 ml of triethylamine and 900 ml of tetrahydrofuran, were slowly added 28 ml of acetyl chloride. After 12 hours at room temperature 50 ml of water were added, the solvent was evaporated, the remaining aqueous phase was extracted with 200 ml of methylene chloride, washed with water, dried on sodium sulfate and the solvent was evaporated. 80 g of raw product were obtained which were dissolved in 1000 ml of alcohol. 1 ml of hydrochloric alcohol 5 N was added and the solution was hydrogenolyzed in the presence of 8 g of palladium on charcoal at 10% in an autoclave, at a temperature of 60° C. and a pressure of 15 bars. Then, it was filtered, the filtrate evaporated and the residue crystallized in ethyl acetate. 52 g of the expected product were thus obtained.
Yield: 77%
NMR spectrum (CDCl3): δppm=6.38, d, (J=7 Hz), amidic protons (—CO—NH—) (exchangeable) Centred on 4.18, m, 1 tropanic proton at 3 3.60, m, tropanic protons at 1 and 5 2.70, s, N—H proton (exchangeable) 1.96, s, 3 acetyl protons (CH3CO—) between 2.20 and 1.15, m, 8 tropanic protons.

By the same process, but using ethyl chloroformiate (instead of acetyl chloride), β-3-ethoxycarbonylamino nor-tropane (VII) was obtained.
Melting point: 252° C.
Empirical formula: C10H19ClN2O2
Molecular weight: 234.72
Elementary analysis:

|  | C | H | N |
|---|---|---|---|
| Calculated (%) | 51.17 | 8.16 | 11.94 |
| Obtained (%) | 50.98 | 8.05 | 11.98 |

NMR spectrum (CDCl3): δppm=
5.55, d, —NH—COO—
4.08, q, and 1.18, t, (J=7 Hz): —COOCH2—CH3
1.96, s,: NH—
3.51, m, tropanic protons at 1 and 5
3.91, m, 1 tropanic proton at 3
centred on 1.72, m, tropanic protons at 2, 4, 6 and 7.

2nd stage: β-3-amino N-p-fluorobenzyl nor-tropane (III)

Code number: 103

A solution of 17 g of β-3-acetamido nor-tropane [(VII) obtained in the preceding stage], of 21 g of p-fluorobenzyl chloride and of 18 ml of triethylamine in 250 ml of acetone was heated to reflux for 12 hours. Then it was filtered, the filtrate was evaporated, and the residue was dissolved in 200 ml of methylene chloride, washed with water, dried on sodium sulfate and the solvent was evaporated. 21 g of raw product were obtained which was dissolved in 250 ml of sulphuric acid at 10% and the solution was heated to reflux for 24 hours. It was washed with 100 ml of methylene chloride, the aqueous solution was alkalized with concentrated potash, extracted with methylene chloride, dried on sodium sulfate and the solvent was evaporated. 17 g of raw product were obtained, yield 96%, which was used directly in the synthesis of the corresponding compound of formula (I) with code No. 19 and described in Example 1.

NMR spectrum (CDCl$_3$): δppm=
centred on 7.08, m, and 3.52, s, 6H(benzylic)
centred on 3.15, m, tropanic protons at 1 and 5
centred on 2.94, m, 1 tropanic proton at 3
between 2.20 and 1.15, m, 8 tropanic protons
1.11, s, NH$_2$ (exchangeable).

By the same process, but from β-3-ethoxycarbonylamino nor-tropane (VII) described in the preceding stage, the β-3-amino N-parafluorobenzyl nor-tropane (III) of code number 103 was also obtained.

By the same process, but from the corresponding reagents, the β-3-amino N-nor-tropanes of formula (III) were obtained. Apart from the few compounds of formula (III) given in table III, the majority of the compounds (III) were used raw (after checking by thin layer chromatography) in the synthesis of the corresponding compounds of formula (I).

TABLE III

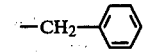

(III)

| Code No. | R | Form | Empirical formula | Molecular weight | Melting point (°C.) | Yield (%) | Elementary analysis - NMR spectrum - IR spectrum |
|---|---|---|---|---|---|---|---|
| 98 | 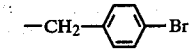 —CH$_2$— | dimaleate | C$_{22}$H$_{28}$N$_2$O$_8$ + 4.5 H$_2$O | 462.87 | 150 | 59 | Elementary analysis:<br>　　　　C　　　H　　　N<br>Cal. (%)　57.08　6.45　6.05<br>Obt. (%)　57.14　6.19　5.92 |
| 99 |  —CH$_2$—◯—Br | base | C$_{14}$H$_{19}$BrN$_2$ | 295.22 | oil | 63 | NMR (CDCl$_3$) δ ppm = 7.32, m, and 3.48, s,<br>6 H CH$_2$—◯—Br<br>= 3.15, m : H at 1 and 5<br>= 2.94, m : H at 3<br>between 2,20 and 1.25, m, H at 2,4,6 and 7,<br>= 1.10, s, NH$_2$ |
| 100 | 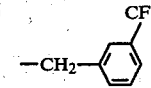 —CH$_2$—◯—CF$_3$ | " | C$_{15}$H$_{19}$F$_3$N$_2$ | 284.32 | oil | 71 | NMR (CDCl$_3$) δ ppm = 7.51, m, and 3.59, s, 6H<br>CF$_3$<br>CH$_2$—◯ ;<br>= 3.15, m, H at 1 and 5;<br>= 2.92 : H at 3;between 2.20 and 1.15, m :<br>= H at 2,4,6 and 7<br>= 1.17, s, : NH$_2$ |
| 101 | 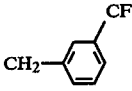 —CH$_2$—◯—Br | " | C$_{14}$H$_{19}$BrN$_2$ | 295.22 | oil | 52 | NMR (CDCl$_3$) δ ppm = 7.47, m, and 3.58,s, 6H<br>Br<br>CH$_2$—◯<br>3.15, m, and 2.95, m, H at 1,3 and 5<br>= between 2.20 and 1.50, m, H at 2,4,6 and 7<br>= 1.42, s, : NH$_2$ |
| 102 | 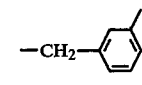 —CH$_2$—◯—F | " | C$_{14}$H$_{19}$FN$_2$ | 234.31 | oil | 66 | NMR (CDCl$_3$) δ ppm = 7.10, m, and 3.55,s, : 6H<br>F<br>CH$_2$—◯<br>= 3.15, m,and 2.94, m : H at 1,3 and 5<br>= between 2.20 and 1.18,m, H at 2,4,6 and 7<br>= 1.14, s, NH$_2$ |
| 103 | 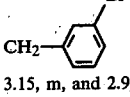 —CH$_2$—◯—F | " | C$_{14}$H$_{19}$FN$_2$ | 234.31 | oil | 96 | NMR (CDCl$_3$) δ ppm = 7.08,m, and 3.52,s, : 6H<br>CH$_2$—◯—F<br>= 3.15,m : H at 1 and 5<br>= 2.94,m : H at 3<br>= between 2.20 and 1.15,m ; H at 2,4,6 and 7 |

TABLE III-continued

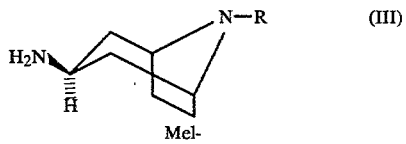

| Code No. | R | Form | Empirical formula | Molecular weight | Melting point (°C.) | Yield (%) | Elementary analysis - NMR spectrum - IR spectrum |
|---|---|---|---|---|---|---|---|
| | | | | | | | = 1.11, s, : NH$_2$ |

The derivatives of formula (I) were tested on laboratory animals and showed neuroleptic properties.

These properties were demonstrated on mice particularly by the test of antagonism to apomorphine straightening, carried out in accordance with the method described by G. GOURET et alia in J. Pharmacol. (Paris) 1973, 4, 341.

The effective doses 50 (ED 50) obtained by intraperitoneal administration, in accordance with the above-mentioned test, of the derivatives of formula (I) and SULPIRIDE chosen as reference compound, are given in table IV below.

Acute toxicity was studied on mice by intraperitoneal administration, and the estimated lethal dose in accordance with the method described by MILLER and THINTER Proc. Soc. Exper. Biol. Med. 1944, 57, 261, are also shown in table IV.

TABLE IV

| Tested compound | Acute toxicity (mice LD 50 mg/kg/i.p.) | Amomorphine straightening ED 50 (mg/kg/i.p.) |
|---|---|---|
| SULPIRIE | 170 | 37 |
| 3 | 300 | 0.04 |
| 8 | 220 | 0.035 |
| 9 | 240 | 0.01 |
| 10 | 325 | 0.035 |
| 16 | 240 | 0.01 |
| 19 | 90 | 0.010 |
| 20 | >400 | 0.034 |
| 21 | 85 | 0.07 |
| 22 | 140 | 0.021 |
| 23 | >400 | 0.07 |
| 24 | 160 | 0.05 |
| 25 | 100 | 0.03 |
| 26 | 140 | 0.011 |
| 27 | >400 | 0.034 |
| 28 | >400 | 0.12 |
| 29 | 180 | 0.012 |
| 30 | 230 | 0.3 |
| 32 | 140 | 0.05 |
| 33 | >400 | 0.19 |
| 35 | 80 | 0.07 |
| 37 | 170 | 0.16 |
| 40 | 130 | 0.05 |
| 41 | 225 | 0.03 |
| 42 | 61 | 0.05 |
| 43 | 120 | 0.03 |
| 48 | 310 | 0.21 |
| 49 | 120 | 0.08 |
| 51 | 140 | 0.03 |
| 60 | 75 | 0.027 |
| 61 | 80 | 0.02 |
| 62 | 60 | 0.04 |
| 64 | 83 | 0.008 |
| 67 | 100 | 0.038 |
| 68 | 47 | 0.02 |
| 71 | 120 | 0.11 |
| 72 | 110 | 0.04 |
| 73 | 170 | 0.02 |
| 74 | 250 | 0.035 |
| 75 | >400 | 0.021 |
| 83 | 140 | 0.031 |

As the results given in this table show, the difference between effective doses and lethal doses 50 is sufficient to allow the derivatives of formula (I) to be used in therapeutics.

These latter are particularly prescribed in the treatment of disturbances of the psychism.

They will be administered orally in the form of tablets, pills or capsules containing 50 to 300 mg of active ingredient (3 to 8 per day), in solution form containing 0.1 to 1% of active ingredient (10 to 40 drops once to thrice per day), by parenteral administration in the form of injectable ampoules containing 5 to 100 mg of active ingredient (3 to 8 ampoules per day).

We claim:

1. A compound having the formula

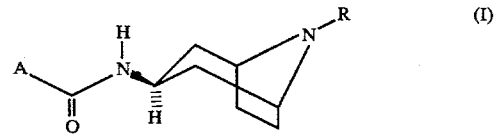

in which R and ACO are selected from the following combinations:
  1. R is 2-methyl thiophene or 3-methyl thiopene, and ACO is 2-methoxy-4-amino-5-bromobenzoyl, and
  2. R is 2-methyl thiophene, 3-methyl thiophene or 2-methyl furan, and ACO is 2-methoxy-4-amino-5-chlorobenzoyl, and pharmacologically acceptable acid addition salts thereof.

2. A compound as claimed in claim 1 in which R is 2-methyl thiophene and ACO is 2-methoxy-4-amino-5-bromobenzoyl.

3. A compound as claimed in claim 1 in which R is 3-methyl thiophene and ACO is 2-methoxy-4-amino-5-bromobenzoyl.

4. A compound as claimed in claim 1 in which R is 2-methyl thiophene and ACO is 2-methoxy-4-amino-5-chlorobenzoyl.

5. A compound as claimed in claim 1 in which R is 3-methyl thiophene and ACO is 2-methoxy-4-amino-5-chlorobenzoyl.

6. A compound as claimed in claim 1 in which R is 2-methyl furan and ACO is 2-methoxy-4-amino-5-chlorobenzoyl.

* * * * *